United States Patent
Yang et al.

(10) Patent No.: US 9,243,265 B2
(45) Date of Patent: Jan. 26, 2016

(54) **RECOMINANT *RALSTONIA EUTROPHA* CAPABLE OF PRODUCING POLYACTIC AND ACID OR POLYLATIC ACID POLYMER, AND METHOD FOR PRODUCING POLYACTIC ACID OR POLYLATIC ACID COPOLYMER USING THE SAME**

(71) Applicant: LG CHEM, LTD., Seoul (KR)

(72) Inventors: Taek Ho Yang, Daejeon (KR); Si Jae Park, Daejeon (KR); Eun Jeong Lee, Daejeon (KR); Hye Ok Kang, Daejeon (KR); Tae Wan Kim, Daejeon (KR); Sang Hyun Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/133,072

(22) Filed: Dec. 18, 2013

(65) Prior Publication Data

US 2014/0242650 A1 Aug. 28, 2014

Related U.S. Application Data

(63) Continuation of application No. 13/147,572, filed as application No. PCT/KR2010/000653 on Feb. 3, 2010, now Pat. No. 8,685,701.

(30) Foreign Application Priority Data

Feb. 5, 2009 (KR) ........................ 10-2009-0009256

(51) Int. Cl.
| | |
|---|---|
| C12N 1/20 | (2006.01) |
| C12N 9/10 | (2006.01) |
| C12N 15/00 | (2006.01) |
| C12P 7/62 | (2006.01) |
| C07H 21/04 | (2006.01) |
| C12N 9/04 | (2006.01) |

(52) U.S. Cl.
CPC ................. *C12P 7/62* (2013.01); *C12N 9/0006* (2013.01); *C12N 9/1029* (2013.01); *C12N 9/13* (2013.01); *C12P 7/625* (2013.01); *C12Y 101/01036* (2013.01); *C12Y 208/03001* (2013.01)

(58) Field of Classification Search
None
See application file for complete search history.

(56) References Cited

U.S. PATENT DOCUMENTS

| 7,186,541 B2 | 3/2007 | Gokarn |
| 2004/0067576 A1 | 4/2004 | Honma |
| 2007/0277268 A1 | 11/2007 | Cho et al. |
| 2008/0038801 A1 | 2/2008 | Maruyama |

FOREIGN PATENT DOCUMENTS

| JP | 2007-228894 | 9/2007 |
| JP | 2008-541719 | 11/2008 |
| KR | 10-2006-0121555 | 11/2006 |
| WO | 2004-024876 | 3/2004 |
| WO | 2006/126796 | 11/2006 |
| WO | 2007/029213 | 3/2007 |
| WO | 2008/062995 | 5/2008 |
| WO | 2008/062999 A1 | 5/2008 |
| WO | 2009/022797 | 2/2009 |

OTHER PUBLICATIONS

"A New Metabolic Link Between Fatty Acids de Novo Synthesis and Polyhroxyalkanoic Acid Synthesis"; Rehn, et al.; The Journal of Biological Chemistry; vol. 273, No. 27 Issue of Sep. 11, pp. 24044-24051, 1999.
Genetic Characterization of Accumulation of Polyhydroxyalkanoate from Styrene in Psdudomonas Putida CA-3; Leary, et al.; Applied and Environmental Microbiology, Aug. 2005; p. 4380-4387.
Enzymatic and Whole-Cell Synthesis of Lactate Containing Polyesters: Toward the Complete Biological Production of Polylactate; Matsumoto, et al; Appl Microbiol Biotechnol (2010) 85: 921-932.
Luengo et al. "Bioplastics from microorganisms", Current Opinion in Microbiology. 2003, vol. 6. No. 3, pp. 251-260.
S. Taguchi, et al., "A microbial factory for lactate-based polyesters using a lactate-polymerizing enzyme.", PNAS, Nov. 11, 2008, vol. 105, No. 45, pp. 17323-17327.
K. Matsumoto & S. Taguchi, "Enzymatic and whole-cell synthesis of lactate-containing polyesters: toward the complete biological production of polylactate.", Appl Microbiol Biotechnol (2010), Epub Dec. 10, 2009, vol. 85, No. 4, pp. 921-932.
N.D. O'Leary, et al., "Genetic Characterization of Accumulation of Polyhydroxyalkanoate from Styrene in Pseudomonas putida CA-3.", Applied and Environmental Microbiology, Aug. 2005, vol. 71, No. 8, pp. 4380-4387.
T.H. Yang, et al., "Biosynthesis of Polylactic Acid and Its Copolymers Using Evolved Propionate CoA Transferase and PHA Synthase.", Biotechnol Bioeng., Jan. 1, 2010, vol. 105, No. 1, pp. 150-160.

*Primary Examiner* — Iqbal H Chowdhury
(74) *Attorney, Agent, or Firm* — Dentons US LLP (57) ABSTRACT

Provided are a recombinant *Ralstonia eutropha* capable of producing polylactate or a hydroxyalkanoate-lactate copolymer, and a method of preparing polylactate or a hydroxyalkanoate-lactate copolymer using the same. The recombinant *Ralstonia eutropha*, which is prepared by introducing a gene of an enzyme converting lactate into lactyl-CoA and a gene of a polyhydroxyalkanoate (PHA) synthase using lactyl-CoA as a substrate thereto, may be cultured, thereby efficiently preparing a lactate polymer and a lactate copolymer.

13 Claims, 3 Drawing Sheets

RECOMINANT *RALSTONIA EUTROPHA* CAPABLE OF PRODUCING POLYACTIC AND ACID OR POLYLATIC ACID POLYMER, AND METHOD FOR PRODUCING POLYACTIC ACID OR POLYLATIC ACID COPOLYMER USING THE SAME

This application is a continuation of U.S. application Ser. No. 13/147,572, filed Aug. 2, 2011, which is a National Stage Entry of International Application No. PCT/KR2010/000653, filed on Feb. 3, 2010, and claims priority to Korean Patent Application No. 10-2009-0009256 filed Feb. 5, 2009, each of which is hereby incorporated by reference in its entirety as if fully set forth herein.

TECHNICAL FIELD

The present invention relates to a recombinant *Ralstonia eutropha* capable of producing polylactate or a hydroxyalkanoate-lactate copolymer and a method of preparing polylactate or a hydroxyalkanoate-lactate copolymer using the same.

BACKGROUND ART

Polylactate (PLA) is a common biodegradable polymer derived from lactate that is highly applicable to the synthesis of general-purpose or medical polymers. Today, polymerization of lactates produced by microbial fermentation is a method for synthesizing PLA. However, this direct polymerization of lactates can only produce PLA with low molecular weight (1000 to 5000 daltons). PLA with a molecular weight of 100,000 daltons or more may be polymerized from smaller PLA molecules produced by the direct polymerization of lactates using a chain coupling agent. However, this method adds some complications to the process due to the addition of a solvent or chain coupling agent, both of which are difficult to remove. The most widely used method of producing high molecular weight PLA includes the conversion of lactate into lactide as well as the synthesis of PLA using the ring-opening polyaddition of lactide rings.

When PLA is synthesized from lactate, producing a PLA homopolymer is easy. However, it is difficult to synthesize PLA copolymers that have various compositions of monomers and very ineffective in a commercial aspect.

Polyhydroxyalkanoate (PHA) is polyester that acts as an energy or carbon storage molecule in microorganisms when there are excessive levels of carbon but a lack of other nutrients such as phosphorus, nitrogen, magnesium and oxygen. PHA is known as an alternative to conventional synthetic plastic due to its similarity to conventional synthetic polymer derived from petroleum as well as its perfect biodegradability.

To produce PHA from microorganisms, there must be present an enzyme that converts the metabolic product of the microorganism into PHA monomer as well as PHA synthase, which then synthesizes PHA polymer from PHA monomers. To synthesize PLA and PLA copolymer using microorganisms, a system as described above is needed, as well as enzymes capable of providing lactyl-CoA and hydroxyacyl-CoA, which is originally a substrate for PHA synthase.

Further, for economical production of biodegradable polymer, it is crucial to efficiently accumulate PLA and PLA copolymer in the cell. In particular, it is necessary to produce a high concentration of PLA and PLA copolymer through high concentration cultivation. Thus, technology that allows the efficient production of a recombinant microorganism compatible with the conditions described above is needed.

DISCLOSURE

Technical Problem

The objective of the present invention is the development of a recombinant *Ralstonia eutropha* (*R. eutropha*) capable of producing a high-concentration polylactate or hydroxyalkanoate-lactate copolymer and a method of preparing polylactate or a hydroxyalkanoate-lactate copolymer using the same.

Technical Solution

One aspect of the present invention is a recombinant strain of *R. eutropha* capable of producing a high concentration of polylactate polymer or copolymer as well as a method of preparing polylactate or hydroxyalkanoate-lactate copolymer using said strain.

The inventors succeeded in synthesizing polylactate polymer and copolymer using propionyl-CoA transferase derived from *Clostridium propionicum* (*C. propionicum*) that produces lactyl-CoA as well as a *Pseudomonas* sp. 6-19-derived mutant of polyhydroxyalkanoate synthase that uses the newly synthesized lactyl-CoA as a substrate (Korean Patent Application No. 10-2006-0116234).

Furthermore, the inventors intended to prepare a recombinant strain of *R. eutropha* capable of efficiently producing polylactate polymer for the economical production of a biodegradable polymer. To this end, the inventors prepared a recombinant *R. eutropha* having lost PHA production capability, and a transformed recombinant *R. eutropha* by transforming the recombinant *R. eutropha* with a plasmid expressing propionyl-CoA transferase derived from *C. propionicum* and a polyhydroxyalkanoate synthase of *Pseudomonas*. sp. 6-19 or introducing a gene expressing a propionyl-CoA transferase derived from *C. propionicum* and a gene expressing a polyhydroxyalkanoate synthase of P. sp. 6-19 to a recombinant *R. eutropha* having lost PHA production capability. The inventors found that polylactate polymer and copolymer could be efficiently prepared from glucose using the recombinant *R. eutropha* as prepared above. This entails the present invention.

Advantageous Effects

The present invention includes a recombinant strain of *Ralstonia eutropha* (*R. eutropha*) capable of efficiently producing polylactate or hydroxyalkanoate-lactate copolymer as well as a method of preparing polylactate or hydroxyalkanoate-lactate copolymer by culturing this same strain.

MODE FOR INVENTION

The present invention provides a recombinant strain of *R. eutropha* that can produce polylactate or a hydroxyalkanoate-lactate copolymer, such that the polyhydroxyalkanoate (PHA) biosynthesis gene operon of wild-type *Ralstonia eutropha* is removed and the gene of the enzyme converting foreign lactate to lactyl-CoA along with the gene of PHA synthase whose substrate is lactyl-CoA is introduced.

In the present invention, the gene of the enzyme converting lactate to lactyl-CoA may be that of propionyl-CoA transferase (pct).

In one particular embodiment, the pct gene can be derived from *C. propionicum*.

In the present invention, the pct gene may be a mutant form that encodes propionyl-CoA transferase with equal or superior lactyl-CoA producing activity.

In one particular embodiment, the pct gene may have the following nucleotide sequences: the nucleotide sequence (cppct) of SEQ ID NO: 1; the nucleotide sequence (cppct512) of SEQ ID NO: 1 containing the A1200G mutation; the nucleotide sequence (cppct522) of SEQ ID NO: 1 containing the T78C, T669C, A1125G, and T1158C mutations; the nucleotide sequence (cppct531) of SEQ ID NO: 1 containing the A1200G mutation whose corresponding amino acid sequence contains the Gly335Asp mutation; the nucleotide sequence (cppct532) of SEQ ID NO: 1 containing the A1200G mutation whose corresponding amino acid sequence contains the Ala243Thr mutation; the nucleotide sequence (cppct533) of SEQ ID NO: 1 containing the T669C, A1125G, and T1158C mutations whose corresponding amino acid sequence contains the Asp65Gly mutation; the nucleotide sequence (cppct534) of SEQ ID NO: 1 containing the A1200G mutation whose corresponding amino acid sequence contains the Asp257Asn mutation; the nucleotide sequence (cppct535) of SEQ ID NO: 1 containing the T669C, A1125G, and T1158C mutations whose corresponding amino acid sequence contains the Asp65Asn mutations; the nucleotide sequence (cppct537) of SEQ ID NO: 1 containing the T669C, A1125G, and T1158C mutations whose corresponding amino acid sequence contains the Thr199Ile mutation; and the nucleotide sequence (cppct540) of SEQ ID NO: 1 containing the T78C, T669C, A1125G, and T1158C mutations whose corresponding amino acid sequence contains the Val193Ala mutation.

The pct gene mutants may be prepared by the method disclosed in Korean Patent Application No. 10-2007-0081855. In one particular embodiment, the pct gene preferably have the nucleotide sequence (cppct540) of SEQ ID NO: 1 containing the T78C, T669C, A1125G, and T1158C mutations whose corresponding amino acid sequence contains the Val193Ala mutation.

Meanwhile, in the present invention, the gene of PHA synthase using lactyl-CoA as its substrate may be the PHA synthase gene of *Pseudomonas* sp. 6-19.

In the present invention, the gene of PHA synthase using lactyl-CoA as its substrate includes a mutant thereof that encodes PHA synthase having equal or superior PHA synthesizing capability.

In one particular embodiment, the gene of PHA synthase using lactyl-CoA as its substrate may possess, but is not limited to, a nucleotide sequence corresponding to the amino acid sequence of SEQ ID NO: 2 or the amino acid sequence of SEQ ID NO: 2 with at least one of the following mutations: E130D, S325T, L412M, S477R, S477H, S477F, S477Y, S477G, Q481M, Q481K and Q481R.

Mutation of the gene encoding PHA synthase using lactyl-CoA as its substrate may be performed by the method disclosed in Korean Patent Application No. 10-2008-0068607. In one particular embodiment, the PHA synthase gene have the nucleotide sequence corresponding to at least one amino acid sequence selected from the group consisting of: the amino acid sequence (C1335) of SEQ ID NO: 2 containing the E130D, S325T, L412M, S477G and Q481M mutations; the amino acid sequence (C1310) of SEQ ID NO: 2 containing the E130D, S477F and Q481K mutations; and the amino acid sequence (C1312) of SEQ ID NO: 2 containing the E130D, S477F and Q481R mutations.

In the present invention, the recombinant strain of *R. eutropha* may further include a gene coding 3HB-CoA synthase. The gene encoding 3HB-CoA synthase allows the preparation of hydroxyalkanoate-lactate copolymer with a high molar fraction of hydroxyalkanoate, even when hydroxyalkanoate is not present in the medium.

In one particular embodiment, the gene coding 3HB-CoA synthase may include a ketothiolase gene and acetoacetyl-CoA reductase gene, both of which may be derived from, but not limited to *R. eutropha*. In the present invention, recombinant *R. eutropha* may furthermore include a PhaG gene.

In one particular embodiment, the PhaG gene may be derived from *P. Putida* KT2440. When the PhaG gene is also included in recombinant *R. eutropha*, recombinant *R. eutropha* becomes capable of producing a hydroxyalkanoate-lactate copolymer of MCL.

Introduction of the gene encoding the enzyme that converts lactate to lactyl-CoA, the gene of PHA synthase that uses lactyl CoA as a substrate, the gene encoding 3HB-CoA synthase and/or the PhaG gene of recombinant *R. eutropha* may be performed by following a conventional method mentioned in the prior art. For example, the method may include preparation of a vector containing the gene encoding the enzyme that converts lactate to lactyl-CoA and/or the gene of PHA synthase that uses lactyl-CoA as a substrate as well as transformation of *R. eutropha* in which a wild-type PHA synthesis operon is removed from the recombinant vector.

The term "vector" implies a DNA construct containing a DNA sequence operably linked to a control sequence capable of expressing DNA in a suitable host. In the present invention, the vector may be a plasmid vector, bacteriophage vector, cosmid vector or Yeast Artificial Chromosome (YAC) vector, although a plasmid vector is typically used. For example, a typical plasmid vector used herein may have (a) a replication origin for effective replication into several hundreds of plasmid vectors per host cell, (b) an antibiotic resistance gene for the selection of a host cell transformed by the plasmid vector, and (c) a restriction enzyme cutting site into which a foreign DNA fragment can be inserted. Although there is no suitable restriction enzyme cutting site, the vector may be easily ligated with foreign DNA using a synthetic oligonucleotide adaptor or linker following conventional methods.

As shown in the prior art, to increase the expression of a transformed gene, the corresponding gene should be operably linked to an expression control sequence that is involved in transcription and translation in the selected expression host. Preferably, the expression control sequence and corresponding gene are included in a single expression vector containing both a bacterial selectable marker and replication origin. When the expression host is a eukaryotic cell, the expression vector should further include a useful expression marker.

The term "expression control sequence" implies a DNA sequence that is essential for the expression of an operably linked coding sequence in a specific host. The control sequence includes a promoter for initiating transcription, a random operator sequence for controlling transcription, a sequence for coding a suitable mRNA ribosome binding site (RBS), and a sequence for controlling the termination of transcription and translation. For example, a control sequence suitable for a prokaryote cell includes a promoter, a random operator sequence, and an mRNA RBS. A control sequence suitable for a eukaryotic cell includes a promoter, a polyadenylation signal, and an enhancer. The promoter is the most critical factor that affects the gene expression in a plasmid. Therefore, a high-expression promoter such as the SRα promoter or cytomegalovirus-derived promoter may be used.

To express a DNA sequence using the present invention, any one of the various expression control sequences may be employed in a vector. Examples of useful expression control sequences include the early and late promoters of SV40 or adenovirus as well as lac system, trp system, TAC system, TRC system, T3 and T7 promoters, the major operator and promoter regions of phage λ, the control region of the fD coat protein, the promoter of the 3-phosphoglycerate kinase gene or that of a different glycolytic enzyme, the promoters of phosphatase genes, e.g., Pho5, a promoter of the yeast α-mating system, and other sequences with configurations or derivations known to control the expression of prokaryotic and eukaryotic cells or their viruses, and various combinations thereof.

Nucleic acid becomes "operably linked" to a nucleotide sequence when both are in a functional relationship. An appropriate molecule (e.g., a transcription-activating protein) may be the product of a gene and control sequence(s) that became linked in such a manner that enables gene expression. For example, the DNA encoding a pre-sequence or secretory leader is operably linked to the DNA encoding a polypeptide when expressed as a pre-protein that participates in the secretion of said polypeptide; a promoter or enhancer that affects the transcription of a coding sequence is operably linked to said coding sequence; and an RBS that affects the transcription or translation of a coding sequence is operably linked to said coding sequence. In general, "operably linked" implies that DNA sequences that are linked together are contiguous. Specifically, regarding the secretory leader, "operably linked" implies that DNA sequences are contiguous and in reading frame. However, an enhancer in contact with the coding sequence is not required. Linkage between sequences may be performed by ligation at a convenient restriction enzyme site. However, a synthetic oligonucleotide adaptor or linker may be used according to conventional methods when there is no restriction enzyme site.

It should be noted that not all vectors and expression control sequences do function equally in the expression of DNA sequences according to the present invention. Similarly, all hosts do not function equally in the same expression system. However, those of ordinary skill in the art may be able to select various vectors, expression control sequences, and hosts without deviating from the scope of the present invention or increasing experimental error. For example, a vector must be selected by considering the host. In addition, on should consider the number of copies of the vector, the ability to control the number of copies, and the expression of other proteins encoded by the corresponding vector, such as an antibiotic marker. Considering these variables, those of ordinary skill in the art may be able to determine suitable combinations of vectors, expression control sequences and hosts.

The present invention also provides a method for preparation of polylactate or a hydrolxyalkanoate-lactate copolymer, culture of a recombinant R. eutropha in medium containing a carbon source and lactate, or a carbon source, lactate and hydroxyalkanoate, and recovery of polylactate or hydroxyalkanoate-lactate copolymer from recombinant R. eutropha.

For example, when cultured in glucose-containing medium or medium containing glucose and hydroxyalkanoate, recombinant R. eutropha will produce either polylactate or a hydroxyalkanoate-lactate copolymer, respectively. However, when recombinant R. eutropha expresses a gene encoding 3HB-CoA synthase, hydroxyalkanoate-lactate copolymer can be prepared with a high molar fraction of hydroxyalkanoate, even when the medium is deficient in hydroxyalkanoate. When recombinant R. eutropha expresses PhaG, a hydroxyalkanoate-lactate copolymer of MCL can be prepared.

The hydroxyalkanoate-lactate copolymer may include, but is not limited to, poly(3HA-co-LA), poly(3HB-co-LA), poly(3HP-co-LA), poly(3HB-co-4HB-co-LA), poly(3HP-co-4HB-co-LA), poly(3HB-co-3HV-co-LA), poly(4HB-co-LA-co-3HP), and poly(MCL 3-HA-co-LA).

Specifically, the yield of hydroxyalkanoate-lactate copolymer may vary according to the type of hydroxyalkanoate contained in the medium.

According to the present invention, the hydroxyalkanoate substrate for the synthesis of hydroxyalkanoate-lactate copolymer may be at least one of the following compounds: 3-hydroxybutyrate, 3-hydroxyvalerate, 4-hydroxybutyrate, medium-chain-length (D)-3-hydroxycarboxylic acid with 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxypentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis dodecenoic acid, 3-hydroxy-5-cis tetradecenoic acid, 3-hydroxy-7-cis tetradecenoic acid, 3-hydroxy-5,8-cis-cis tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methyl ester, 3-hydroxyadipinic acid-methyl ester, 3-hydroxysuberic acid-methyl ester, 3-hydroxyazelaic acid-methyl ester, 3-hydroxysebacic acid-methyl ester, 3-hydroxysuberic acid-ethyl ester, 3-hydroxysebacic acid-ethyl ester, 3-hydroxypimelic acid-propyl ester, 3-hydroxysebacic acid-benzyl ester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethylheptenoic acid.

The present invention provides a novel method for the preparation of polylactate or hydroxyalkanoate-lactate copolymer using a recombinant strain of *Ralstonia eutropha*.

Exemplary embodiments of the present invention have been disclosed herein. Although specific terms are employed, they are to be interpreted only in a generic and descriptive sense and not for the purpose of limitation. Accordingly, it should be understood by those of ordinary skill in the art that various changes in form and detail are possible without deviating from the spirit and scope of the present invention as set forth in the following claims.

EXAMPLES

Example 1

Preparation of *R. eutropha* Having Lost PHA Production Capability

To remove the PHA biosynthesis gene operon involved in the synthesis of poly(3-hydroxybutyrate)[P(3HB)] in *Ralstonia eutropha* (*R. eutropha*), a recombinant vector was prepared as follows.

A DNA fragment containing the PHB-producing operon derived from *R. eutropha* H16 was cleaved from the pSYL105 vector (Lee et al., Biotech. Bioeng., 1994, 44:1337-1347) by BamHI/EcoRI and inserted into the BamHI/EcoRI recognition site of pBluescript II (Stratagene), thereby producing pReCAB recombinant vector.

PHA synthase (phaC$_{RE}$) along with monomer-supplying enzymes (phaA$_{RE}$ & phaB$_{RE}$) were constantly expressed in a pReCAB vector under the PHB operon promoter. It is known that this vector also effectively operates in *E. coli* (Lee et al., Biotech. Bioeng., 1994, 44:1337-1347). The new pReCAB vector was cleaved with BstBI/NdeI to remove the genes encoding *R. eutropha* H16 PHA synthase (phaC$_{RE}$), b-ketothiolase (phaA$_{RE}$) and acetoacetyl-CoA reductase (phaB$_{RE}$). A GFP gene amplified from a pEGFP plasmid (BD Biosciences Clontech) by PCR was then inserted into the vector (pΔCAB-GFP).

EGFP_F_BstBI aaaaattcgaaac aggaaacagaat atggtgagcaag (SEQ ID NO: 3)

EGFP_R_NdeI ggaattcCATATGttacttgtacagctcgtcca (SEQ ID NO: 4)

The pΔCAB-GFP vector was next cleaved with BamHI/XhoI, thereby producing a gene segment to which the *R. eutropha* PHA biosynthesis promoter was attached in the 5' direction and to which a transcription terminator gene was attached in the 3' direction. The gene segment was inserted into a pK18mobSacB vector (Schafer et al. Gene (1994) 145: 69-73) cleaved with BamHI/SalI, thereby producing the pK18-ΔCAB-GFP vector. Since the pK18mobSacB vector can express sacB, a recombinant microorganism was prepared by inserting a foreign gene into the chromosome using sucrose.

Figure 1:
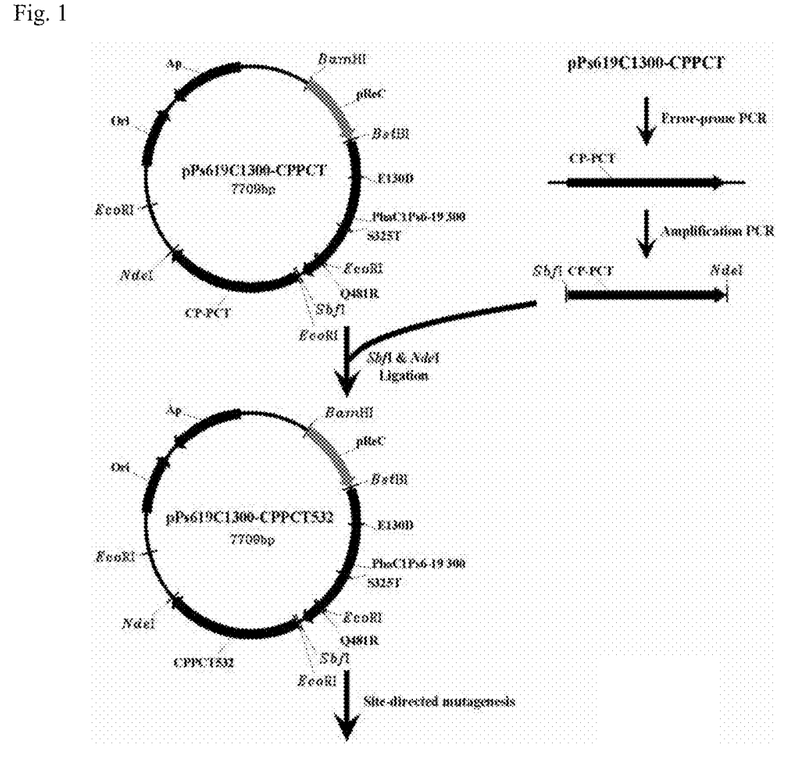
FIGS. 1 and 2 illustrate the process of preparing a recombinant expression vector containing the mutant gene of polyhydroxyalkanoate synthase derived from *Pseudomonas* sp. 6-19, the mutant gene of propionyl-CoA transferase derived from *C. propionicum*, and a phaAB gene derived from *R. eutropha*.
Figure 2:
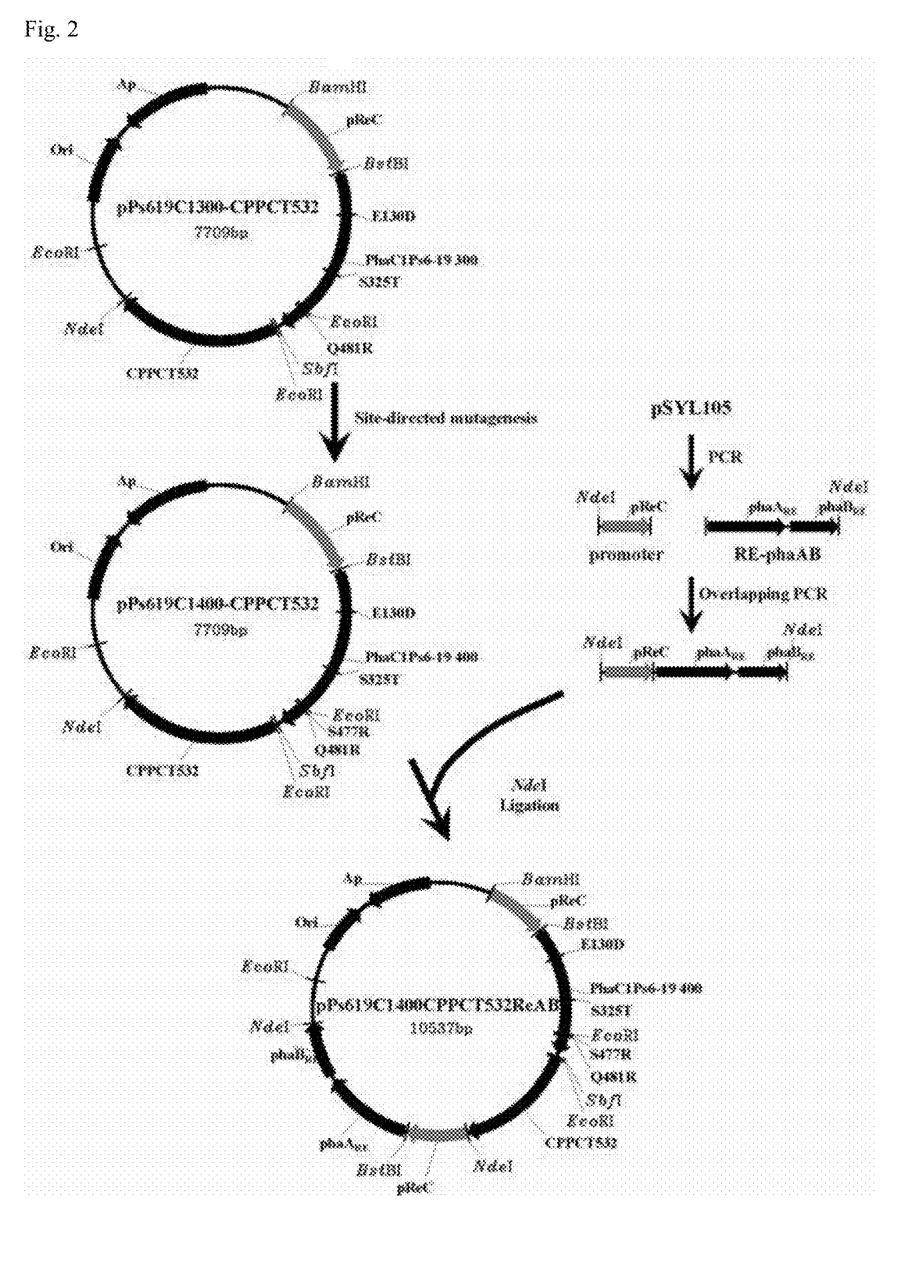
Figure 3:
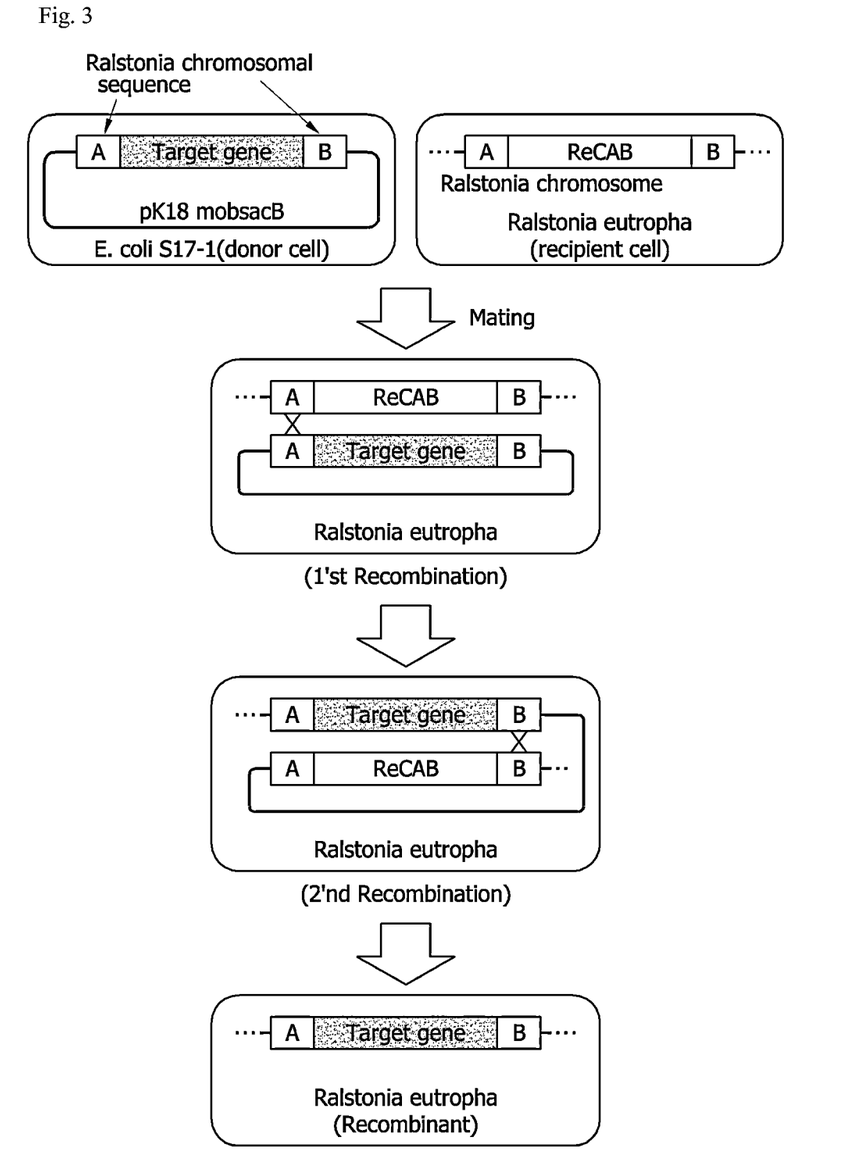
FIG. 3 illustrates a process of mating between *Escherichia coli* 517-1 and *R. eutropha* as well as the insertion of a target gene into the chromosome of *R. eutropha* to prepare recombinant *R. eutropha*.

After the pK18-ΔCAB-GFP vector was transformed to *E. coli* S17-1, the S17-1 (pK18-ΔCAB-GFP) was cultured in an LB liquid medium containing 25 mg/l kanamycin at 37° C. for 24 hours. *R. eutropha* NCIMB11599 was also cultured in an LB liquid medium at 30° C. for 24 hours. These culture solutions were mixed with each other to have a volume ratio of the S17-1 (pK18-ΔCAB-GFP) to the *R. eutropha* NCIMB11599 of 3:1, and added drop by drop to an LB solid medium by 100 ul. The resulting plate was cultured in a static incubator at 30° C. for 18 hours. During the culture, mating occurred, in which the pK18-ΔCAB-GFP vector of the S17-1 was transferred to *Ralstonia eutropha*, resulting in, as shown in FIG. 3, a first crossover at a homology site of chromosomal DNA of *Ralstonia*. Since the pK18-ΔCAB-GFP is impossible to be replicated in *R. eutropha*, when the pK18-ΔCAB-GFP was normally inserted into the chromosome of *R. eutropha* through the first crossover between genes, *R. eutropha* showed resistance to the plate containing 500 mg/L kanamycin.

A colony in which the pK18-ΔCAB-GFP was inserted into the chromosome of *R. eutropha* through the first crossover was selected by suspending the cells mated in the LB plate in an LB liquid medium, and plating the suspension on a plate containing 500 mg/L kanamycin and 35 mg/l chloramphenicol. For a second crossover, the recombinant *R. eutropha* in which the first crossover was done was cultured in an LB liquid medium at 30° C. for 24 hours, and then 100 ul of the culture solution was plated on an LB plate containing 70 g/L sucrose. *R. eutropha* in which the second crossover occurred by a sacB gene was selected as recombinant *R. eutropha* through PCR (see FIG. 3). After the second crossover was normally done, the recombinant *R. eutropha* lost the PHA biosynthesis operon (phaCAB), but the GFP gene remained in the chromosome. Through colony PCR, the recombinant *R. eutropha* in which the GFP was normally inserted into the chromosome was found, and was called as *R. eutropha* GFP.

Example 2

Preparation of Recombinant *R. eutropha* into which PHA Synthase from *Pseudomonas* sp. 6-19 (KCTC 11027BP) and Propionyl-CoA Transferase (CPPCT) from *Clostridium propionicum* are Inserted The pK18-ΔCAB-GFP vector prepared in Example 1 was cleaved with BamHI/NdeI to remove GFP, and a gene segment obtained by cleaving a pPs619C1335CPPCT540 vector with BamHI/NdeI was inserted thereinto, thereby preparing a pK18-ΔCAB-335540 vector. By using the vector, a recombinant *R. eutropha* 335540, in which phaCAB was removed and phaC1$_{Ps6-19}$335 from *Pseudomonas* sp. 6-19 (KCTC 11027BP) and propionyl-CoA transferase (CPPCT540) from *Clostridium propionicum* were inserted into a chromosome, was prepared (see Table 1). The preparing process was performed in the same manners as Example 1 using *E. coli* S17-1 (see FIG. 3).

TABLE 1

| Recombinant *R. eutropha* | Recombinant plasmid used herein |
| --- | --- |
| *R. eutropha* NCIMB11599 | |
| *R. eutropha* GFP | pK18-ΔCAB-GFP |
| *R. eutropha* 335540 | pK18-ΔCAB-335540 |
| *R. eutropha* 335ReAB | pK18-ΔCAB-335ReAB |
| *R. eutropha* 310540ReAB | pK18-ΔCAB-310540ReAB |
| *R. eutropha* 312540ReAB | pK18-ΔCAB-312540ReAB |

Example 3

Preparation of Recombinant *R. eutropha* into which PHA Synthase from *Pseudomonas* sp. 6-19 (KCTC 11027BP) and Ketothiolase (phaA$_{RE}$) and Acetoacetyl-CoA Reductase (phaB$_{RE}$) from *R. eutropha* H16 are Inserted The pK18-ΔCAB-GFP vector prepared in Example 1 was cleaved with BamHI/NdeI to remove GFP, and a gene segment obtained by cleaving pPs619C1335ReAB vector with BamHI/NdeI was inserted thereinto, thereby preparing pK18-ΔCAB-335ReAB vector. By using the vector, a recombinant *R. eutropha* 335ReAB, in which phaCAB was removed and phaC1$_{Ps6-19}$335 from *Pseudomonas* sp. 6-19 (KCTC 11027BP) and PHB monomer-supplying enzymes (phaA$_{RE}$ & phaB$_{RE}$) from *R. eutropha* H16 were inserted into a chromosome, was prepared (see Table 1). The preparing process was performed in the same manners as Example 1 using *E. coli* S17-1 (see FIG. 3).

Example 4

Preparation of Recombinant *R. eutropha* into which PHA Synthase from *Pseudomonas* sp. 6-19 (KCTC 11027BP), Propionyl-CoA Transferase (CPPCT) from *Clostridium propionicum*, and Ketothiolase (phaA$_{RE}$) and Acetoacetyl-CoA Reductase (phaB$_{RE}$) from *R. eutropha* H16 are Inserted The pK18-ΔCAB-GFP vector prepared in Example 1 was cleaved with BamHI/NdeI to remove GFP, and gene segments obtained by cleaving pPs619C1310CPPCT540ReAB and pPs619C1312CPPCT540ReAB vectors with BamHI/NdeI were inserted thereinto, thereby preparing pK18-ΔCAB-310540ReAB and pK18-ΔCAB-312540ReAB vectors, respectively. By using these vectors, recombinant *R. eutropha* 310540ReAB and *R. eutropha* 312540ReABphaCAB, in which phaCAB was removed and phaC1$_{Ps6-19}$310 or phaC1$_{Ps6-19}$312 from *Pseudomonas* sp. 6-19 (KCTC 11027BP), propionyl-CoA transferase (CPPCT540) from *Clostridium propionicum*, and PHB monomer-supplying enzymes (phaA$_{RE}$ & phaB$_{RE}$) from *R. eutropha* H16 were inserted into a chromosome, were prepared (see Table 1). The preparing process was performed in the same manners as Example 1 using *E. coli* S17-1 (see FIG. 3).

Example 5

Biosynthesis of P(3HB-co-LA) Copolymer through Culture of Recombinant *R. eutropha*

The recombinant *R. eutropha* shown in Table 1 was cultured in a minimal medium containing glucose as a basic substrate and 34 ug/mL chloramphenicol, resulting in biosynthesis of a P(3HB-co-LA) copolymer. The composition of the minimal medium was as follows (per L; KH$_2$PO$_4$, 2.65 g; Na$_2$HPO$_4$, 3.8 g; NH$_4$Cl, 0.72 g; MgSO$_4$7H$_2$O, 0.4 g; Tracer, 1 mL). In addition, the composition of tracers was as follows (per L; FeSO$_4$.7H$_2$O, 10 g; ZnSO$_4$.7H$_2$O, 2.25 g; CuSO$_4$.5H$_2$O, 1 g; MnSO$_4$.5H$_2$O, 0.5 g; CaCl$_2$.2H$_2$O, 2 g; Na$_2$B$_4$O$_7$.7H$_2$O, 0.23 g; (NH$_4$)$_6$Mo$_7$O$_{24}$, 0.1 g; 35% HCl, 10 mL). Prior to a main culture, a seed culture was performed in an LB medium containing antibiotics for 30 hours. The seed-culture solution was inoculated to the minimal medium containing a substrate and antibiotics to have a concentration of 1% for the main culture for 4 days. All cultures were performed at 30° C. at a speed of 200 rpm. After the culture was completed, a cell lysate was harvested by centrifugation. The harvested cell lysate was dried in a drier at 80° C. for 48 hours, and analyzed by gas chromatography to measure the content of the P(3HB-co-LA) copolymer accumulated in the cell lysate. The result is shown in Table 2. Reference materials used in the analysis were P(3HB-co-12 mol % 3HV) copolymer and PLA polymer.

TABLE 2

Biosynthesis of P(3HB-co-LA) copolymer through culture of recombinant *R. eutropha*

| Recombinant *R. eutropha* | Substrate | P(3HB-co-LA) (wt %) | LA mol % |
|---|---|---|---|
| *R. eutropha* 335540 | 2% glucose | 24.33 | 0.00 |
|  | 2% glucose, 3HB* | 47.73 | 0.00 |
|  | 2% glucose, NaL$^+$ | 7.72 | 31.71 |
|  | 2% glucose, 3HB, NaL$^+$ | 25.20 | 16.18 |
| *R. eutropha* 310540ReAB | 2% glucose | 46.33 | 0.05 |
|  | 1.5% glucose, NaL$^{++}$ | 24.06 | 8.64 |
| *R. eutropha* 312540ReAB | 2% glucose | 46.50 | 0.06 |
|  | 1.5% glucose, NaL$^{++}$ | 12.87 | 7.18 |
|  | NaL$^{+++}$ | 17.97 |  |

*3HB: 3-hydroxybutyrate, 2 g/L
$^+$NaL: Sodium lactate (pH 7), 4 g/L
$^{++}$NaL: Sodium lactate (pH 7), 6 g/L
$^{+++}$NaL: Sodium lactate (pH 7), 24 g/L

Example 6

Biosynthesis of P(3HB-co-LA-co-mcl3HA) Copolymer Through Culture of Recombinant *R. eutropha*

The *R. eutropha* GFP was transformed to a vector expressing PHA synthase from *Pseudomonas* sp. 6-19 (KCTC 11027BP), propionyl-CoA transferase (CPPCT) from *Clostridium propionicum*, and PhaG from *P. putida* KT2440, and then cultured as described in Example 5. As a carbon source, 2% glucose was used. The content of a copolymer accumulated in a cell lysate is shown in Table 3.

A process of preparing a vector was as follows.

To begin with, a phaG gene amplified from *P. putida* KT2440 by PCR was inserted into an NdeI site of a pPs619C1300CPPCT532 or pPs619C1334CPPCT532 vector (pPs619C1300CPPCT532PhaG or pPs619C1334CPPCT532PhaG). Subsequently, the pPs619C1300CPPCT532PhaG or pPs619C1334CPPCT532PhaG was cleaved with BamHI/XhoI, a gene segment obtained thereby was inserted into the same site of pBBR1MCS2 vector, thereby preparing a recombinant plasmid replicable in *R. eutropha* (pMCS2Ps619C1300CPPCT532PhaG or pMCS2Ps619C1334CPPCT532PhaG). By using the vector, a recombinant *R. eutropha* was prepared.

KTPhaG500f-NdeI ggaattc catatg ggggttggcgccggg ggag (SEQ ID NO: 5)

KTPhaGb-2100-NdeI 5-ggaattc catatg gga tcg gtg ggt aat tgg cc (SEQ ID NO: 6)

TABLE 3

Biosynthesis of P(LA-co-3HB-co-mcl3HA) copolymer through culture of recombinant R. eutropha

| Enzymes in Plasmid | PHA content (wt %) | PHA composition (mol %) | | | | | | |
|---|---|---|---|---|---|---|---|---|
| | | LA (C3) | 3HB (C4) | 3HHx (C6) | 3HO (C8) | 3HD (C10) | 3HDD (C12) | 3H5DD (C12') |
| PhaC1-300$_{Ps6-19}$ Pct532 PhaG | 20.9 | 2.0 | 94.1 | 0.5 | 0.8 | 0.9 | 1.5 | 0.3 |
| PhaC1-334$_{Ps6-19}$ Pct532 PhaG | 19.7 | 2.7 | 91.7 | 0.5 | 1.2 | 1.3 | 2.3 | 0.3 |

The invention claimed is:

1. A recombinant *Ralstonia eutropha* (*R. eutropha*) capable of producing polylactate or a hydroxyalkanoate-lactate copolymer, wherein polyhydroxyalkanoate (PHA) biosynthesis gene operon of a wild-type *R. eutropha* is removed, and a gene of an enzyme converting lactate into lactyl-CoA and a gene of a PHA synthase using lactyl-CoA as a substrate are introduced,
wherein the gene of the enzyme converting lactate into lactyl-CoA is a propionyl-CoA transferase (pct) gene,
wherein the pct gene has a nucleotide sequence corresponding to the nucleotide sequence (cppct532) of SEQ ID NO: 1 comprising the A1200G mutation whose corresponding amino acid sequence comprises the Ala243Thr mutation.

2. The recombinant *R. eutropha* according to claim 1, wherein the pct gene is derived from *Clostridium propionicum*.

3. The recombinant *R. eutropha* according to claim 1, wherein the gene of the PHA synthase using lactyl-CoA as a substrate is derived from *Pseudomonas* sp. 6-19.

4. The recombinant *R. eutropha* according to claim 1, wherein the gene of the PHA synthase using lactyl-CoA as a substrate has a nucleotide sequence corresponding to the amino acid sequence of SEQ ID NO: 2 or the amino acid sequence of SEQ ID NO: 2 with at least one of the following mutations: E130D, S325T, L412M, S477R, S477H, S477F, S477Y, S477G, Q481M, Q481K and Q481R.

5. The recombinant *R. eutropha* according to claim 4, wherein the gene of the PHA synthase using lactyl-CoA as a substrate has a nucleotide sequence corresponding to at least one amino acid sequence selected from the group consisting of:
the amino acid sequence (C1335) of SEQ ID NO: 2 containing the E130D, S325T, L412M, S477G and Q481M mutations;
the amino acid sequence (C1310) of SEQ ID NO: 2 containing the E130D, S477F and Q481 K mutations; and
the amino acid sequence (C1312) of SEQ ID NO: 2 containing the E130D, S477F and Q481R mutations.

6. The recombinant *R. eutropha* according to claim 1, further comprising a gene coding a 3HB-CoA synthase.

7. The recombinant *R. eutropha* according to claim 6, wherein the gene coding the 3HB-CoA synthase includes a ketothiolase gene and an acetoacetyl-CoA reductase gene.

8. The recombinant *R. eutropha* according to claim 7, wherein the ketothiolase gene and the acetoacetyl-CoA reductase gene are derived from the *R. eutropha*.

9. The recombinant *R. eutropha* according to claim 1, which is capable of producing a hydroxyalkanoate-lactate copolymer of Medium Chain Length (MCL).

10. The recombinant R, *eutropha* according to claim 1, further comprising a PhaG gene.

11. The recombinant *R. eutropha* according to claim 10, wherein the PhaG gene is derived from *P. Putida* KT2440.

12. A method of preparing polylactate or a hydroxyalkanoate-lactate copolymer, comprising:
culturing a recombinant *Ralstonia eutropha* of claim 1 in a medium containing a carbon source and lactate, or a carbon source, lactate and hydroxyalkanoate; and
recovering polylactate or a hydroxyalkanoate-lactate copolymer from the recombinant *R. eutropha*.

13. The method according to claim 12, wherein hydroxyalkanoate of the hydroxyalkanoate-lactate copolymer includes at least one selected from the group consisting of 3-hydroxybutyrate, 3-hydroxyvalerate, 4-hydroxybutyrate, medium-chain-length (D)-3-hydroxycarboxylie acid with 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxypentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis dodecenoic acid, 3-hydroxy-5-cis tetradecenoic acid, 3-hydroxy-7-cis tetradecenoic acid, 3-hydroxy-5,8-cis-cis tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methyl ester, 3-hydroxyadipinic acid-methyl ester, 3-hydroxysuberic acid-methyl ester, 3-hydroxyazelaic acid-methyl ester, 3-hydroxysebacic acid-methyl ester, 3-hydroxysuberic acid-ethyl ester, 3-hydroxysebacie acid-ethyl ester, 3-hydroxypimelic acid-propyl ester, 3-hydroxysebacic acid-benzyl ester, 3-hydroxy-8-acetoxyoctanoic acid, 3-hydroxy-9-acetoxynonanoic acid, phenoxy-3-hydroxybutyric acid, phenoxy-3-hydroxyvaleri acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethylheptenoic acid.

\* \* \* \* \*

SEQUENCE LISTING

<160> NUMBER OF SEQ ID NOS: 6

<210> SEQ ID NO 1
<211> LENGTH: 1572
<212> TYPE: DNA
<213> ORGANISM: Clostridium propionicum
<220> FEATURE:
<221> NAME/KEY: gene
<222> LOCATION: (1)..(1572)
<223> OTHER INFORMATION: Propionyl-CoA transferase of Clostridium propionicum

<400> SEQUENCE: 1

```
atgagaaagg ttcccattat taccgcagat gaggctgcaa agcttattaa agacggtgat      60
acagttacaa caagtggttt cgttggaaat gcaatccctg aggctcttga tagagctgta     120
gaaaaaagat tcttagaaac aggcgaaccc aaaaacatta cctatgttta ttgtggttct     180
caaggtaaca gagacggaag aggtgctgag cactttgctc atgaaggcct tttaaaacgt     240
tacatcgctg gtcactgggc tacagttcct gctttgggta aaatggctat ggaaaataaa     300
atggaagcat ataatgtatc tcaggtgca ttgtgtcatt tgttccgtga tatagcttct     360
cataagccag gcgtatttac aaaggtaggt atcggtactt tcattgaccc agaaatggc      420 ggcggtaaag taatgatat taccaaagaa gatattgttg aattggtaga gattaagggt     480
caggaatatt tattctaccc tgcttttcct attcatgtag ctcttattcg tggtacttac     540
gctgatgaaa gcggaaatat cacatttgag aaagaagttg ctcctctgga aggaacttca     600
gtatgccagg ctgttaaaaa cagtggcggt atcgttgtag ttcaggttga agagtagta      660 aaagctggta ctcttgaccc tcgtcatgta aaagttccag gaatttatgt tgactatgtt     720
gttgttgctg acccagaaga tcatcagcaa tctttagatt gtgaatatga tcctgcatta     780
tcaggcgagc atagaagacc tgaagttgtt ggagaaccac ttcctttgag tgcaaagaaa     840
gttattggtc gtcgtggtgc cattgaatta gaaaaagatg ttgctgtaaa tttaggtgtt     900
ggtgcgcctg aatatgtagc aagtgttgct gatgaagaag gtatcgttga ttttatgact     960
ttaactgctg aaagtggtgc tattggtggt gttcctgctg gtggcgttcg ctttggtgct    1020
tcttataatg cggatgcatt gatcgatcaa ggttatcaat tcgattacta tgatggcggc    1080
ggcttagacc tttgctattt aggcttagct gaatgcgatg aaaaaggcaa tatcaacgtt    1140
tcaagatttg gccctcgtat cgctggttgt ggtggtttca tcaacattac acagaataca    1200
cctaaggtat tcttctgtgg tactttcaca gcaggtggct aaaggttaa aattgaagat    1260 ggcaaggtta ttattgttca agaaggcaag cagaaaaat tcttgaaagc tgttgagcag    1320
```

```
attacattca atggtgacgt tgcacttgct aataagcaac aagtaactta tattacagaa    1380
agatgcgtat tccttttgaa ggaagatggt ttgcacttat ctgaaattgc acctggtatt    1440
gatttgcaga cacagattct tgacgttatg gattttgcac ctattattga cagagatgca    1500
aacggccaaa tcaaattgat ggacgctgct ttgtttgcag aaggcttaat gggtctgaag    1560
gaaatgaagt cc                                                        1572
```

<210> SEQ ID NO 2
<211> LENGTH: 559
<212> TYPE: PRT
<213> ORGANISM: Pseudomonas sp. 6-19 (KCTC 11027BP)
<220> FEATURE:
<221> NAME/KEY: PEPTIDE
<222> LOCATION: (1)..(559)
<223> OTHER INFORMATION: PHA synthase of Pseudomonas sp. 6-19
      (KCTC 11027BP)

<400> SEQUENCE: 2

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
                20                  25                  30

Ala Ser Ala Arg Met Val Leu Arg Gln Ala Ile Lys Gln Pro Val His
            35                  40                  45

Ser Val Lys His Val Ala His Phe Gly Leu Glu Leu Lys Asn Val Leu
        50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

```
Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
            325                 330                 335

Leu Phe Val Asn Glu Gln Thr Leu Glu Ala Ala Lys Arg His Ser Tyr
        340                 345                 350

Gln Ala Gly Val Leu Glu Gly Arg Asp Met Ala Lys Val Phe Ala Trp
    355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
            405                 410                 415

Lys Asn Asn Pro Leu Ile Arg Pro Asn Ala Leu Glu Val Cys Gly Thr
        420                 425                 430

Pro Ile Asp Leu Lys Gln Val Thr Ala Asp Ile Phe Ser Leu Ala Gly
    435                 440                 445

Thr Asn Asp His Ile Thr Pro Trp Lys Ser Cys Tyr Lys Ser Ala Gln
450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
            485                 490                 495

Ser Thr Glu Val Ala Glu Asn Ala Asp Glu Trp Gln Ala Asn Ala Thr
        500                 505                 510

Lys His Thr Asp Ser Trp Trp Leu His Trp Gln Ala Trp Gln Ala Gln
    515                 520                 525

Arg Ser Gly Glu Leu Lys Lys Ser Pro Thr Leu Gly Ser Lys Ala
530                 535                 540

Tyr Pro Ala Gly Glu Ala Ala Pro Gly Thr Tyr Val His Glu Arg
545                 550                 555
```

<210> SEQ ID NO 3
<211> LENGTH: 37
<212> TYPE: DNA
<213> ORGANISM: Artificial Sequence
<220> FEATURE:
<223> OTHER INFORMATION: synthesized primer EGFP_F_BstBI

<400> SEQUENCE: 3
aaaaattcga aacaggaaac agaatatggt gagcaag                               37

<210> SEQ ID NO 4
<211> LENGTH: 33
<212> TYPE: DNA
<213> ORGANISM: Artificial Sequence
<220> FEATURE:
<223> OTHER INFORMATION: synthesized primer EGFP_R_NdeI

<400> SEQUENCE: 4
ggaattccat atgttacttg tacagctcgt cca                                   33

<210> SEQ ID NO 5
<211> LENGTH: 32
<212> TYPE: DNA
<213> ORGANISM: Artificial Sequence
<220> FEATURE:

-continued

```
<223> OTHER INFORMATION: synthesized primer KTPhaG500f-NdeI

<400> SEQUENCE: 5
ggaattccat atgggggttg gcgccggggg ag                                    32

<210> SEQ ID NO 6
<211> LENGTH: 33
<212> TYPE: DNA
<213> ORGANISM: Artificial Sequence
<220> FEATURE:
<223> OTHER INFORMATION: synthesized primer KTPhaGb-2100-NdeI 5

<400> SEQUENCE: 6
ggaattccat atgggatcgg tgggtaattg gcc                                   33
```